United States Patent
Jetly

(10) Patent No.: US 11,523,756 B1
(45) Date of Patent: Dec. 13, 2022

(54) DETECTING MIDDLE EAR ABNORMALITIES USING A SMARTPHONE-BASED TYMPANOMETER

(71) Applicant: Anushka Sameer Jetly, Friendswood, TX (US)

(72) Inventor: Anushka Sameer Jetly, Friendswood, TX (US)

( * ) Notice: Subject to any disclaimer, the term of this patent is extended or adjusted under 35 U.S.C. 154(b) by 344 days.

(21) Appl. No.: 16/810,531

(22) Filed: Mar. 5, 2020

Related U.S. Application Data

(60) Provisional application No. 62/814,437, filed on Mar. 6, 2019.

(51) Int. Cl.
*A61B 5/00* (2006.01)
*A61B 5/12* (2006.01)

(52) U.S. Cl.
CPC ............ *A61B 5/126* (2013.01); *A61B 5/0022* (2013.01); *A61B 5/6815* (2013.01); *A61B 5/7435* (2013.01); *A61B 2560/02* (2013.01)

(58) Field of Classification Search
CPC ..... A61B 5/126; A61B 5/0022; A61B 5/6815; A61B 5/7435; A61B 2560/02
USPC .......................................................... 600/559
See application file for complete search history.

(56) References Cited

U.S. PATENT DOCUMENTS

| | | | |
|---|---|---|---|
| 2007/0129649 A1* | 6/2007 | Thornton | A61B 5/121 600/559 |
| 2018/0064374 A1* | 3/2018 | Givens | G16H 40/63 |
| 2019/0046025 A1* | 2/2019 | Oyadiran | A61B 1/227 |

* cited by examiner

*Primary Examiner* — Tanmay K Shah
(74) *Attorney, Agent, or Firm* — Plager Schack LLP; Mark H. Plager; Stephen Hallberg

(57) ABSTRACT

A smartphone and tympanometer-based middle ear abnormality detection mobile system and a method for detecting middle ear abnormalities by a mobile computing device coupled to a tympanometer is disclosed. The method detects middle ear abnormalities by a smartphone-based tympanometer, thereby allowing mobility for medical practitioners to check for middle ear abnormalities in people unable to visit an ENT at a medical facility. The method is implemented as a software application that runs on the mobile computing device and displays results instantly to help determine any of several types of middle ear infection which may be present. This is a huge improvement over existing process where a doctor has to make that determination based on his/her interpretation of the tympanogram.

10 Claims, 5 Drawing Sheets

DETECTING MIDDLE EAR ABNORMALITIES USING A SMARTPHONE-BASED TYMPANOMETER

CLAIM OF BENEFIT TO PRIOR APPLICATION

This application claims benefit to U.S. Provisional Patent Application 62/814,437, entitled "DETECTING MIDDLE EAR ABNORMALITIES USING A SMARTPHONE-BASED TYMPANOMETER," filed Mar. 6, 2019. The U.S. Provisional Patent Application 62/814,437 is incorporated herein by reference.

BACKGROUND

Embodiments of the invention described in this specification relate generally to detecting middle ear infections, and more particularly, to a smartphone and tympanometer-based middle ear abnormality detection mobile system and a method for detecting middle ear abnormalities by a mobile computing device coupled to a tympanometer.

Currently, commercially available tympanometers display a tympanogram that has to be analyzed by an ear, nose and throat ("ENT") specialist. There is no automatic process or routine procedure to analyze the tympanogram, such that a lay person or even a non-ENT medical professional can accurately detect the existence and determine the type of middle ear infection. Furthermore, there is no existing device or system that analyzes a tympanogram other than an ENT specialist.

Many people have access to a general practitioner doctor, and may visit their doctor when they experience ear problems. However, middle ear infections are very difficult to detect visually. Nevertheless, in general practice, many non-ENT medical professionals (such as general practitioner doctors) will visually analyze a patient's ear and, when there is no visual clues of infection, will end up referring the patient to a hearing specialist (as if the problem the patient is experiencing is a loss of hearing). This is a problem for doctors and patients alike, who end up wasting time and performing needless hearing tests when middle ear infections have not been ruled out.

There is also a greater problem for people in remote regions of the world, or in underdeveloped or poverty-stricken areas. Many of those people never see ENT specialists and those who do typically face high travel and expense hurdles in traveling to a medical facility with an ENT and covering costs for treatment. The road of lowest cost is traveled more often, leaving such people at greater risk of having long lasting or chronic undetected/untreated middle ear infections.

Therefore, what is needed is a mobile system in connection with a tympanometer which together can be used by any medical professional, whether ENT or non-ENT, to detect middle ear abnormalities and which is capable of analyzing tympanograms to detect possible middle ear abnormalities.

BRIEF DESCRIPTION

A novel smartphone and tympanometer-based middle ear abnormality detection mobile system and a method for detecting middle ear abnormalities by a mobile computing device coupled to a tympanometer are disclosed. In some embodiments, the method detects middle ear abnormalities by a smartphone-based tympanometer. This allows medical evaluation in remote or underdeveloped regions, thereby allowing medical practitioners to check for middle ear abnormalities in many people who are typically unable to visit an ENT at a medical facility. The method is implemented as a software application that runs on the mobile computing device and displays results instantly to help determine any of several types of middle ear infection which may be present. This is a huge improvement over existing process where a doctor has to make that determination based on his/her interpretation of the tympanogram.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

Figure 1:
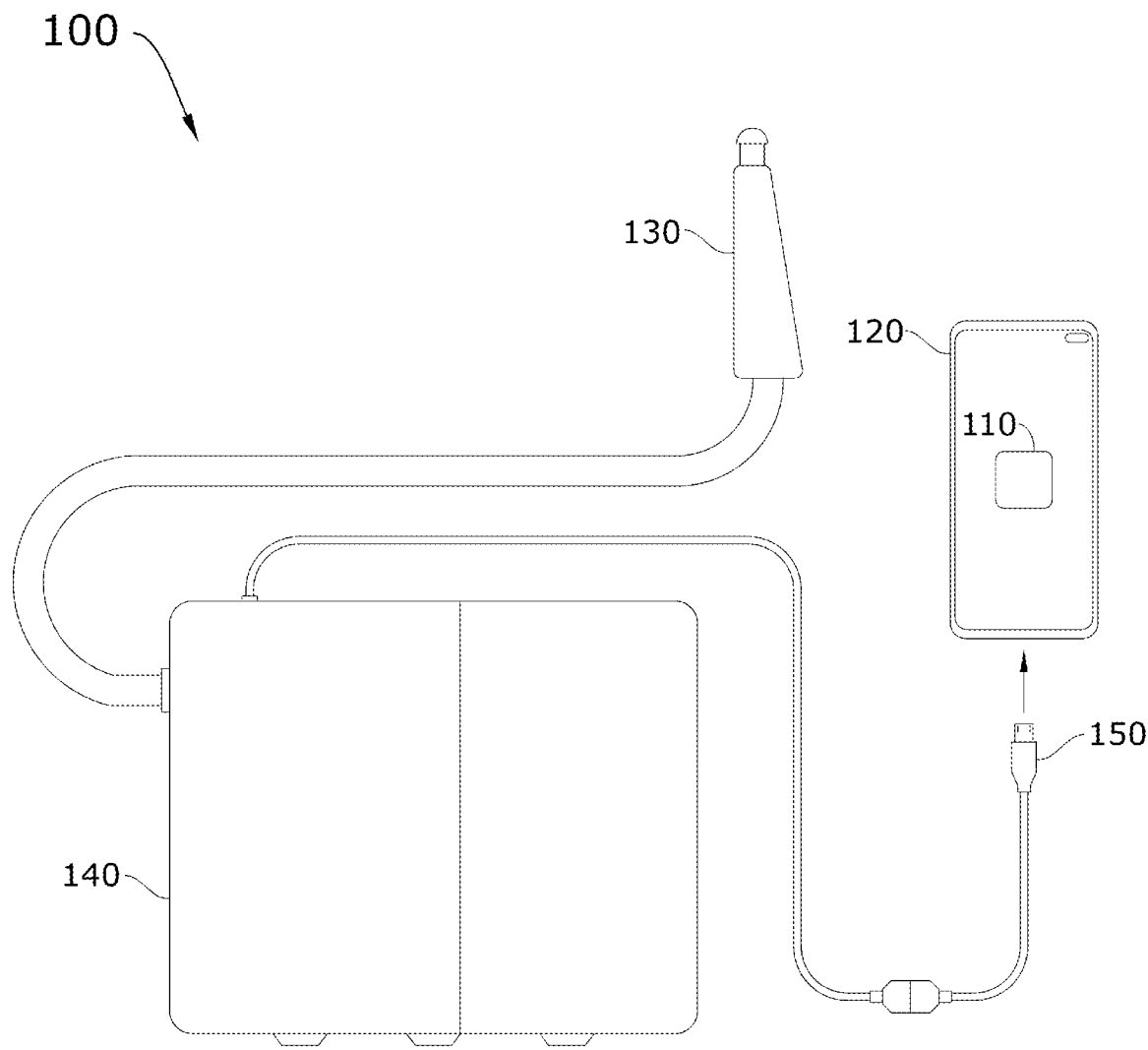
FIG. 1 conceptually illustrates a schematic view of a smartphone and tympanometer-based middle ear abnormality detection mobile system in some embodiments.

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of the invention include a novel smartphone and tympanometer-based middle ear abnormality detection mobile system and a method for detecting middle ear abnormalities by a mobile computing device coupled to a tympanometer. In some embodiments, the method detects middle ear abnormalities by a smartphone-based tympanometer. This allows medical evaluation in remote or underdeveloped regions, thereby allowing medical practitioners to check for middle ear abnormalities in many people who are typically unable to visit an ENT at a medical facility. The method is implemented as a software application that runs on the mobile computing device and displays results instantly to help determine any of several types of middle ear infection which may be present. This is a huge improvement over existing process where a doctor has to make that determination based on his/her interpretation of the tympanogram.

As stated above, currently, commercially available tympanometers display a tympanogram, but there is no existing automatic process or routine procedure to analyze the tympanogram, and thus, the tympanogram normally has to be analyzed by an ENT to accurately detect the existence of middle ear abnormalities and determine the type of abnormality/infection. Since middle ear infections are difficult to detect visually and tympanograms are typically only able to be interpreted by the learned eyes of an ENT, many non-ENT medical professionals refer patients to hearing labs for hearing tests to be performed. Another problem with the conventional approaches to determining middle ear abnormalities is that people in remote regions of the world, or in underdeveloped or poverty-stricken areas typically do not have access to ENT specialists and those who do face high barriers to proper and timely treatment (e.g., arduous travel and/or great expense). Thus, many people are left at greater risk of leaving middle ear infections untreated.

Embodiments of the smartphone and tympanometer-based middle ear abnormality detection mobile system and the method for detecting middle ear abnormalities by a mobile computing device coupled to a tympanometer described in this specification solve such problems by implementation of the method into a software application which builds a tympanogram based on the pressure and sound energy (acoustic compliance) information received from the tympanometer, and displays the resulting tympanogram and provides results in the screen of the mobile computing device. That is, once the tympanogram is built, the software is able to analyze and determine the type of middle ear infection. In addition, some embodiments of the system and method include a machine learning component that helps the application learn the type of middle ear infection if it is shown incorrectly after the analysis.

Embodiments of the smartphone and tympanometer-based middle ear abnormality detection mobile system and the method for detecting middle ear abnormalities by a mobile computing device coupled to a tympanometer described in this specification differ from and improve upon currently existing options. In particular, there is no existing equipment or software application that processes a tympanogram and automatically displays the type of middle ear infection. The smartphone and tympanometer-based middle ear abnormality detection mobile system and the method for detecting middle ear abnormalities by a mobile computing device coupled to a tympanometer described in this disclosure is the first solution in terms of a software application that analyzes and displays the type of middle ear infection.

The smartphone and tympanometer-based middle ear abnormality detection mobile system and the method for detecting middle ear abnormalities by a mobile computing device coupled to a tympanometer of the present disclosure may be comprised of the following elements. This list of possible constituent elements is intended to be exemplary only and it is not intended that this list be used to limit the system and method of the present application to just these elements. Persons having ordinary skill in the art relevant to the present disclosure may understand there to be equivalent elements that may be substituted within the present disclosure without changing the essential function or operation of the system and method.

1. A smartphone with a mobile computing device operating system (e.g., with Android based operating system)

2. A tympanometer with USB terminal and probe for the ear

3. The software application installed on the smartphone

The various elements of the smartphone and tympanometer-based middle ear abnormality detection mobile system and the method for detecting middle ear abnormalities by a mobile computing device coupled to a tympanometer of the present disclosure may be related in the following exemplary fashion. It is not intended to limit the scope or nature of the relationships between the various elements and the following examples are presented as illustrative examples only. The tympanometer (2) is connected to the smartphone (1) via USB cable. The software application (3) is installed on the smartphone (1). Using the tympanometer (2), the readings are obtained and processed by the software (3) on the smartphone (1). In this way, the user is able to know the type of middle ear infection.

By way of example, FIG. 1 conceptually illustrates a schematic view of a smartphone and tympanometer-based middle ear abnormality detection mobile system 100. As shown in this figure, the smartphone and tympanometer-based middle ear abnormality detection mobile system 100 includes a software application 110 installed on a smartphone 120. A mobile computing device operating system (not shown) is also installed on the smartphone 120. The smartphone and tympanometer-based middle ear abnormality detection mobile system 100 also includes a tympanometer device comprising a tympanometer probe 130 and a tympanometer pressure pump and power source 140. A pump tube connects the tympanometer pressure pump and power source 140 to the tympanometer probe 130. The tympanometer pressure pump and power source 140 includes a USB terminal to which a USB cable 150 is connected to deliver data (the readings of the tympanometer) captured by the tympanometer probe 130 to the smartphone 120 for generating and visually outputting a tympanogram of the data and to analyze the data in view of the generated tympanogram.

Figure 2:
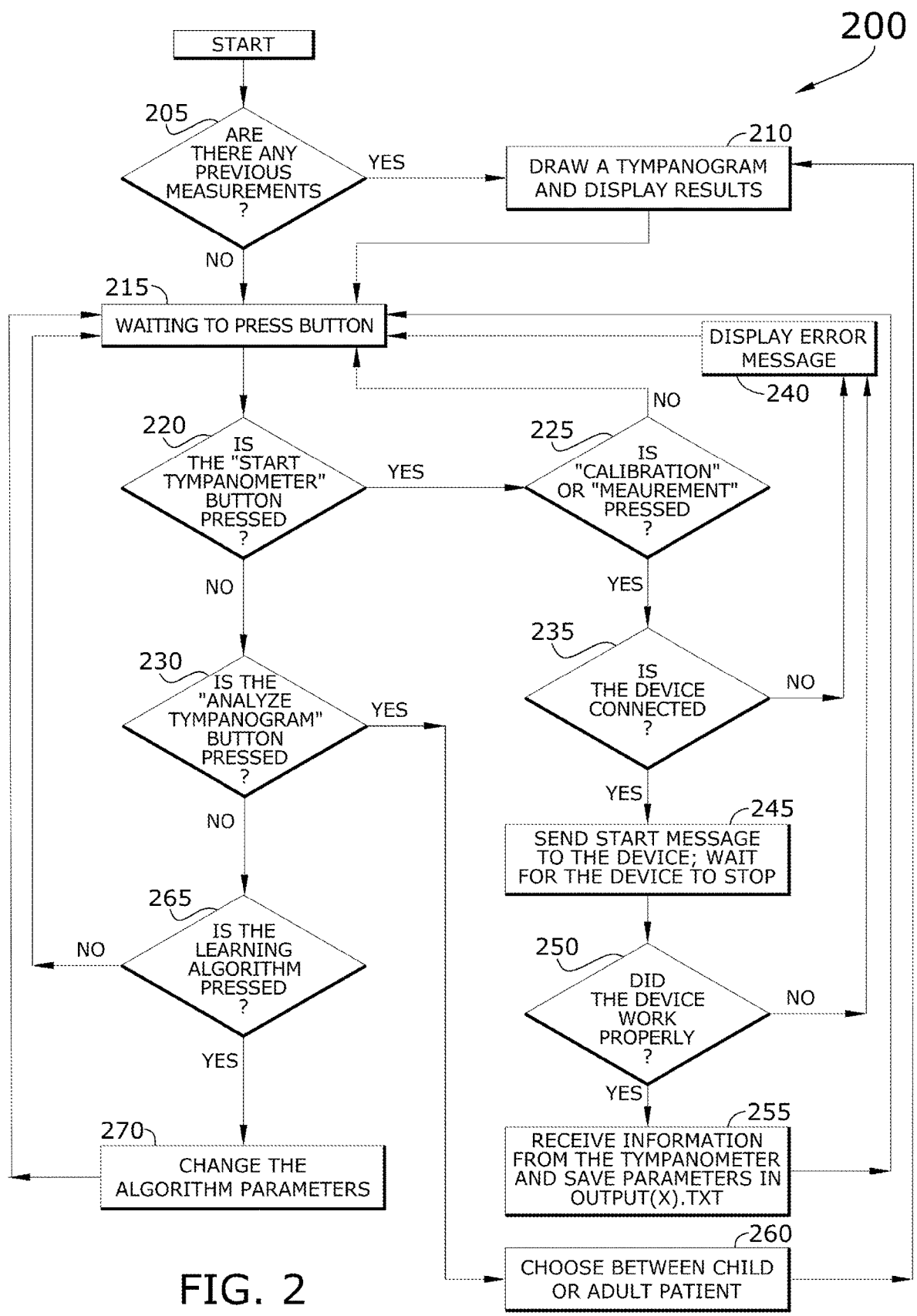
FIG. 2 conceptually illustrates a machine learning method for detecting middle ear abnormalities using a smartphone-based tympanometer in some embodiments.

Turning now to FIG. 2, a method for detecting middle ear abnormalities using a smartphone-based tympanometer is conceptually illustrated. As shown in this figure, the method for detecting middle ear abnormalities using a smartphone-based tympanometer 200 includes several steps. In some embodiments, the method for detecting middle ear abnormalities using a smartphone-based tympanometer 200 starts by determining (at 205) whether there are any previous measurements from the tympanometer. For example, if the tympanometer probe was inserted in the ear canal of a patient and a test was started, then previous tympanometer readings would be available for graphing and analysis. Thus, when there are measurements, the method for detecting middle ear abnormalities using a smartphone-based tympanometer 200 draws (at 210) a tympanogram of the data and visually outputs the results of the readings and displays the tympanogram.

Next, the method for detecting middle ear abnormalities using a smartphone-based tympanometer 200 of some embodiments waits (at 215) for selection of a tympanometer function. In some embodiments, a person using the tympanometer may select a button that starts a tympanometer test or a different button to analyze the tympanogram. In some embodiments, a medical specialist can select another button to change parameters for the machine learning algorithm. For example, an ENT or other medical specialist runs the tympanometer on a patient and a tympanogram is generated which does not make sense to the ENT or medical specialist, who is then able to adjust the machine learning algorithm in accordance with their advanced education, learning, and/or understanding of the results.

While waiting for a button to be pressed, the method for detecting middle ear abnormalities using a smartphone-based tympanometer 200 of some embodiments listens for any button selection. The method for detecting middle ear abnormalities using a smartphone-based tympanometer 200 therefore determines (at 220) whether a tympanometer start button is pressed. In connection with the tympanometer start button being pressed, the method for detecting middle ear abnormalities using a smartphone-based tympanometer 200 determines whether a calibration option or a measurement option is pressed (at 225). When neither the calibration option nor the measurement option is pressed, the method for detecting middle ear abnormalities using a smartphone-based tympanometer 200 simply returns to the step for waiting (at 215) for selection of the tympanometer function. On the other hand, when the calibration option or the measurement option is pressed, then the method for detecting middle ear abnormalities using a smartphone-based tympanometer 200 proceeds to the next step of determining (at 235) whether the tympanometer device is connected, which is described next.

When the device is not connected, the method for detecting middle ear abnormalities using a smartphone-based tympanometer 200 visually outputs an error message (at 240) and then returns to the step for waiting (at 215) for a button to be pressed. On the hand, when the device is determined (at 235) to be connected, then the method for detecting middle ear abnormalities using a smartphone-based tympanometer 200 sends (at 245) a start message to the tympanometer device and then waits for the tympanometer to stop. In some embodiments, when the software application running on the mobile device of the user sends the start message to the tympanometer device, a trigger signal at the tympanometer device starts the test. Next, the method for detecting middle ear abnormalities using a smartphone-based tympanometer 200 of some embodiments determines (at 250) whether the tympanometer device worked properly in relation to the start message. For example, the tympanometer may fail when the tympanometer probe is not sufficiently inserted into the ear canal of the patient and, therefore, generates an error message which informs the software application running on the mobile device that the tympanometer device is not working properly at this moment. Thus, when the tympanometer device is determined (at 250) not to be working properly, the method for detecting middle ear abnormalities using a smartphone-based tympanometer 200 returns back to the step for waiting (at 215) for a button selection to be made by the user. For example, the user can adjust the tympanometer probe and re-run a test. However, when the tympanometer device is determined (at 250) to be working properly, then the method for detecting middle ear abnormalities using a smartphone-based tympanometer 200 receives (at 255) information from the tympanometer device and saves the parameters to a file (such as an "output(x).txt" file or another logically named file). After saving the results of the tympanometer test, the method for detecting middle ear abnormalities using a smartphone-based tympanometer 200 returns to the step for waiting (at 215) for a particular button to be pressed. For example, the user may selection the function for generating and visually outputting the tympanogram of the results just saved.

Turning back to the determination (at 220) of whether the tympanometer start button is pressed, when the tympanometer start button is not pressed, the method for detecting middle ear abnormalities using a smartphone-based tympanometer 200 then determines (at 230) whether an analyze tympanogram button is pressed. For example, after a user runs a tympanometer test of a patient, the user may wish to have the tympanometer readings analyzed and the tympanogram displayed. When the analyze tympanogram button is determined (at 230) to be pressed, the method for detecting middle ear abnormalities using a smartphone-based tympanometer 200 of some embodiments presents an option for the user to choose (at 260) between a child patient or adult patient. In some embodiments, the analysis takes into consideration whether the patient is a child or an adult before analyzing the results and generating the tympanogram. After receiving a selection of either a child patient or an adult patient, the method for detecting middle ear abnormalities using a smartphone-based tympanometer 200 proceeds to the step for drawing (at 210) the tympanogram and displaying results of the analysis. Then the method for detecting middle ear abnormalities using a smartphone-based tympanometer 200 returns to the step for waiting (at 215) for the user to selection of function button.

Now turning back to the determination (at 230) of whether the analyze tympanogram button is pressed, when the button selection (at 215) is not the analyze tympanogram button or the start tympanometer button, then the method for detecting middle ear abnormalities using a smartphone-based tympanometer 200 determines (at 265) whether the learning algorithm button is pressed. When the learning algorithm button is not pressed, the method for detecting middle ear abnormalities using a smartphone-based tympanometer 200 returns to the step for waiting (at 215) for the user to selection of function button. On the other hand, when the learning algorithm button is pressed, the method for detecting middle ear abnormalities using a smartphone-based tympanometer 200 of some embodiments changes (at 270) the machine learning algorithm parameters as specified by the user or in connection with the results. Then the method for detecting middle ear abnormalities using a smartphone-based tympanometer 200 returns to the step for waiting (at 215) for the user to selection of function button. The steps described above are cycled through in various order dependent upon user direction until the user decides to stop running the software application running on the mobile device and/or switch off the power of the tympanometer device.

The smartphone and tympanometer-based middle ear abnormality detection mobile system and the method for detecting middle ear abnormalities by a mobile computing device coupled to a tympanometer of the present disclosure generally works by way of the software building a tympanogram based on pressure and admittance (Compliance) readings received from the tympanometer. The X-axis is pressure reading between −200 and +200 deca Pascal and the Y-axis is admittance measure in mmho. Based on the graph plotted, the readings are compared to the ranges for the different types of middle ear infections which are Type A (normal), Type B, Type C and Type B-High which are all infected. A machine learning component is added. Normally the machine learning result is the same as the normal result but if a specialist feels that a particular result is not the right one, then the application can learn this result so that next time the correct result is displayed.

After setup is complete and the reading from the tympanometer are received by the application, the tympanogram is plotted. The readings of the tympanogram which are the admittance (compliance) values at different pressure readings are compared to the range of values for each type of middle ear infection. Based on which range the readings fall into, the type of infection is determined.

To use the smartphone and tympanometer-based middle ear abnormality detection mobile system and the method for detecting middle ear abnormalities by a mobile computing device coupled to a tympanometer of the present disclosure, a user may connect a simple tympanometer that has a USB output to a mobile computing device (such as an Android based smartphone) that has the tympanogram application. The tympanometer probe is inserted into the ear of the patient and the tympanometer returns the readings back to the application. The application builds a graph based on the readings and compares the readings from this graph with certain known limits to determine the type of infection. This helps the user who is not necessarily a doctor to understand the type of infection or the lack of.

Figure 3:
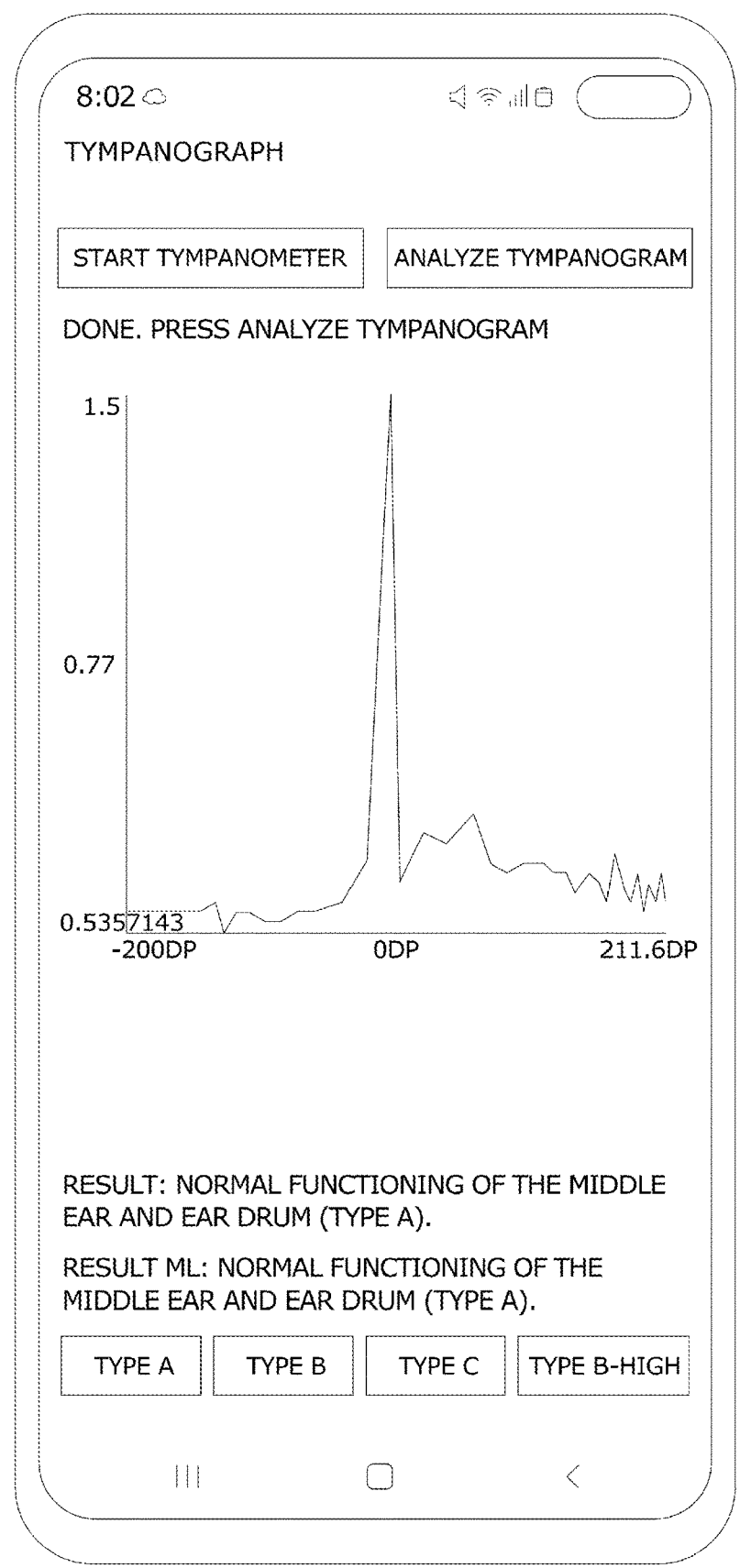
FIG. 3 conceptually illustrates a first exemplary user interface (UI) of output generated by a mobile app that detects middle ear abnormalities when used in connection with a smartphone-based tympanometer in some embodiments.

By way of example, FIG. 3 conceptually illustrates an exemplary user interface (UI) of the software application that runs on the mobile device of the user in connection with a tympanometer device with a first tympanogram and analysis of the readings from a tympanometer test of a patient 300. As shown in this figure, the exemplary UI of the software application includes a start tympanometer button, an analyze tympanogram button, an image of a tympanogram that is visually output based on the readings of a tympanometer test of the patient, tympanometer analysis results in text format, and several machine learning parameter buttons that allow an ENT or specialist to change the parameters of the machine learning algorithm in view of the analyzed results of the tympanometer test readings of the patient. In this case, for instance, the tympanometer analysis results in text format are shown as being normal "Type A" output.

Figure 4:
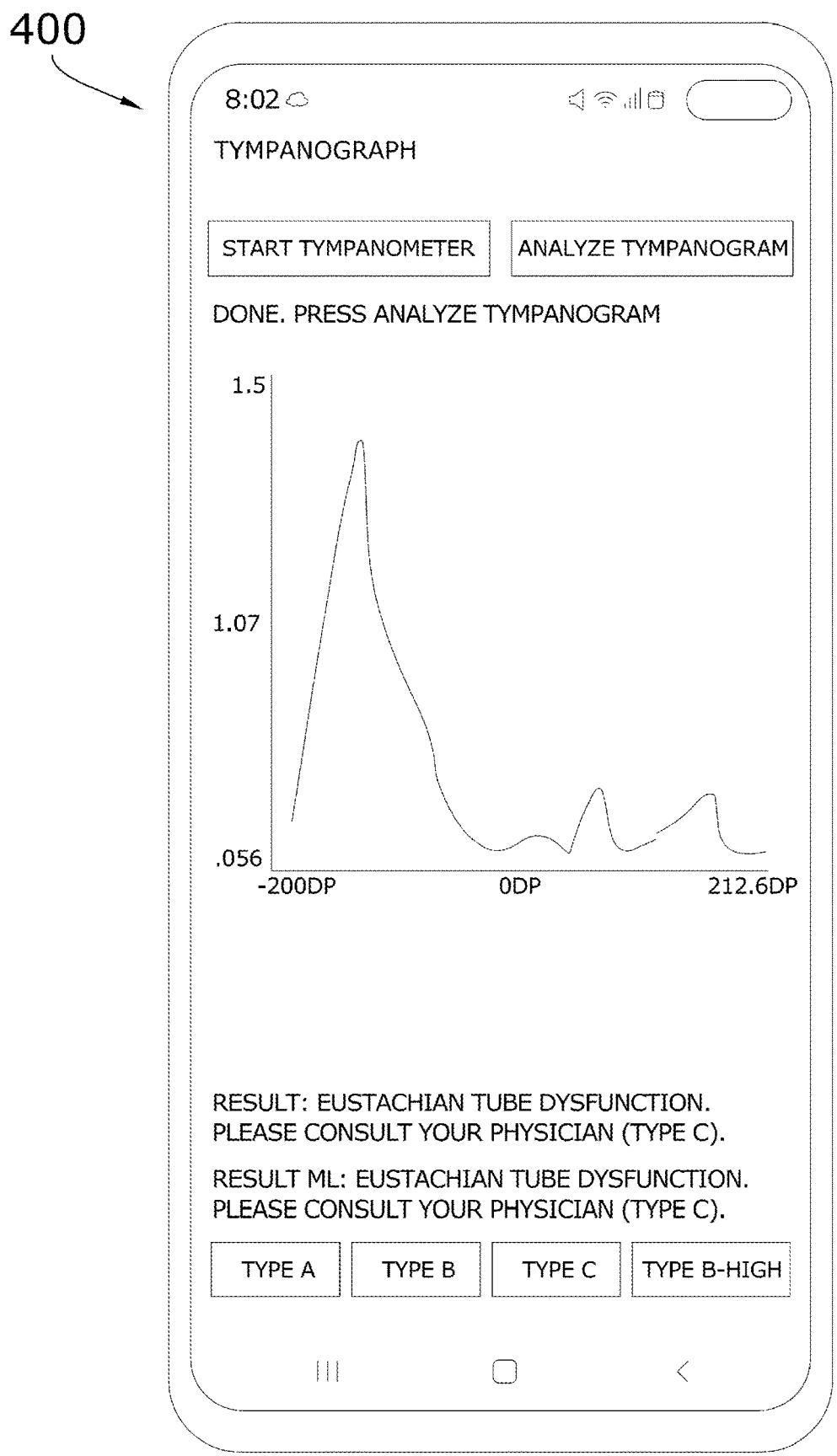
FIG. 4 conceptually illustrates a second exemplary user interface (UI) of output generated by a mobile app that detects middle ear abnormalities when used in connection with a smartphone-based tympanometer in some embodiments.

By comparison, FIG. 4 conceptually illustrates the exemplary UI of the software application that runs on the mobile device of the user in connection with the tympanometer device with a second tympanogram and analysis of the readings from a tympanometer test of a patient 400. In this case, for instance, the tympanometer analysis results in text format identify dysfunction of eustachian tube for the patient, noted as "Type C" output. Again, an ENT or specialist with advanced knowledge, education, training, or experience could trigger a change to the machine learning algorithm if the analysis results are incorrect.

The above-described embodiments of the invention are presented for purposes of illustration and not of limitation. Also, many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, solid state drives (SSDs), EPROMs, etc. The computer readable media does not include carrier waves and electronic signals passing wirelessly or over wired connections.

In this specification, the terms "software", "software program", and "software application" are meant to include firmware residing in read-only memory or applications stored in magnetic storage, which can be read into memory for processing by a processor. Also, in some embodiments, multiple software inventions can be implemented as subparts of a larger program while remaining distinct software inventions. In some embodiments, multiple software inventions can also be implemented as separate programs. Finally, any combination of separate programs that together implement a software invention described here is within the scope of the invention. In some embodiments, the software programs, when installed to operate on one or more electronic systems, define one or more specific machine implementations that execute and perform the operations of the software programs.

Figure 5:
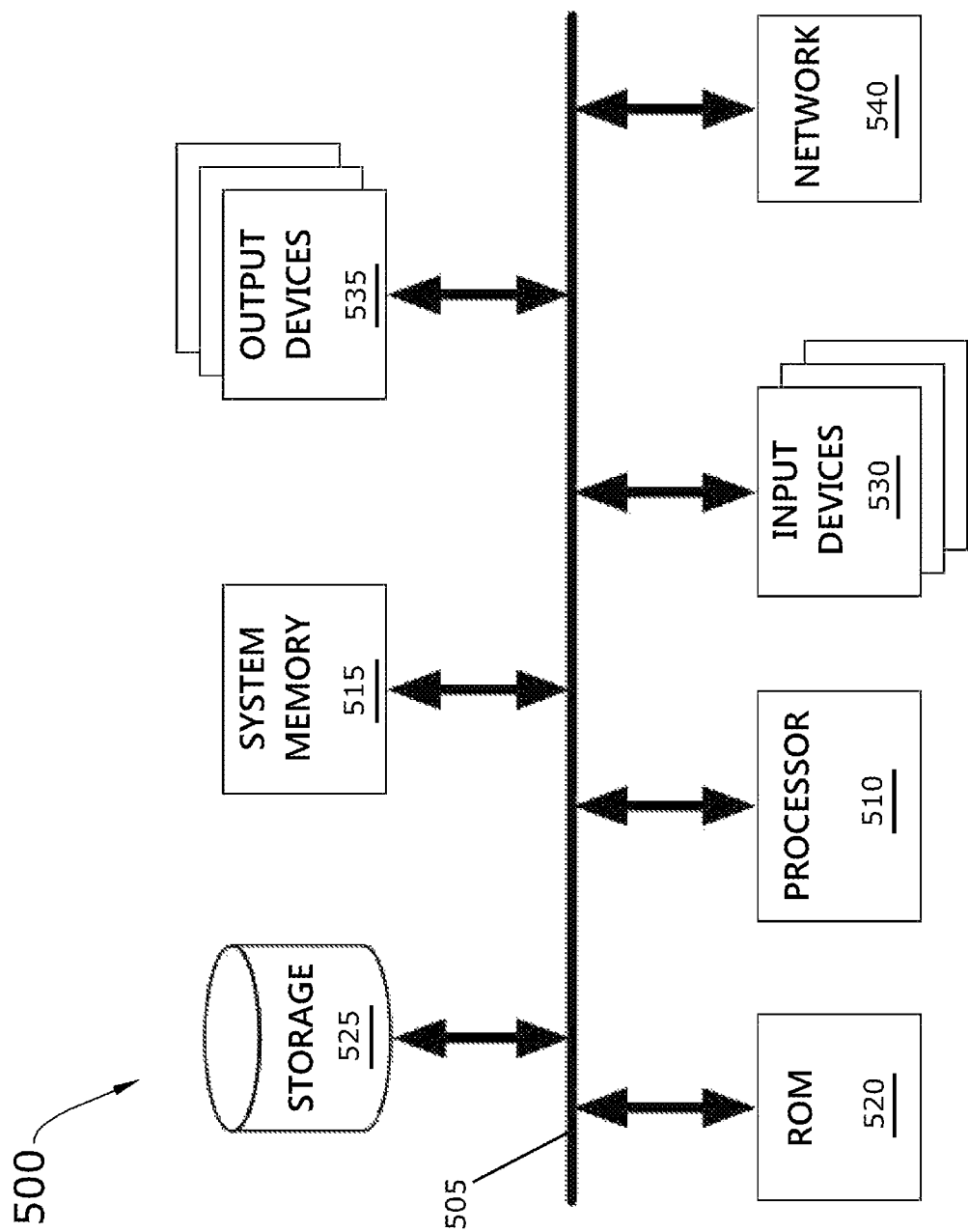
FIG. 5 conceptually illustrates an electronic system with which some embodiments of the invention are implemented.

FIG. 5 conceptually illustrates an electronic system 500 with which some embodiments of the invention are implemented. The electronic system 500 may be a computer, phone (cell phone, mobile phone, smartphone, etc.), PDA (iPod, other handheld computing device, etc.), tablet computing device, or any other sort of electronic device or computing device. Such an electronic system includes various types of computer readable media and interfaces for various other types of computer readable media. Electronic system 500 includes a bus 505, processing unit(s) 510, a system memory 515, a read-only-memory 520, a permanent storage device 525, input devices 530, output devices 535, and a network 540. Where implementation occurs on a mobile computing device (such as those noted above including, without limitation, a smartphone mobile communication device), the electronic system components of a mobile device bus, mobile device processing unit(s), a mobile device system memory, a mobile device read-only memory, a mobile device permanent storage device, a tympanometer input device, a mobile device display screen output device, and a wireless network are referred to the same elements of the bus 505, the processing unit(s) 510, the system memory 515, the read-only-memory 520, the permanent storage device 525, the input devices 530, the output devices 535, and the network 540 for the sake of readability and so as to not obscure the description with unnecessary detail.

The bus 505 collectively represents all system, peripheral, and chipset buses that communicatively connect the numerous internal devices of the electronic system 500. For instance, the bus 505 communicatively connects the processing unit(s) 510 with the read-only 520, the system memory 515, and the permanent storage device 525.

From these various memory units, the processing unit(s) 510 retrieves instructions to execute and data to process in order to execute the processes of the invention. The processing unit(s) may be a single processor or a multi-core processor in different embodiments.

The read-only-memory (ROM) 520 stores static data and instructions that are needed by the processing unit(s) 510 and other modules of the electronic system. The permanent storage device 525, on the other hand, is a read-and-write memory device. This device is a non-volatile memory unit that stores instructions and data even when the electronic system 500 is off. Some embodiments of the invention use a mass-storage device (such as a magnetic or optical disk and its corresponding disk drive) as the permanent storage device 525.

Other embodiments use a removable storage device (such as a flash drive) as the permanent storage device 525. Like the permanent storage device 525, the system memory 515 is a read-and-write memory device. However, unlike storage device 525, the system memory 515 is a volatile read-and-write memory, such as a random access memory. The system memory 515 stores some of the instructions and data that the processor needs at runtime. In some embodiments, the invention's processes are stored in the system memory 515, the permanent storage device 525, and/or the read-only 520. For example, the various memory units include instructions for processing appearance alterations of displayable characters in accordance with some embodiments. From these various memory units, the processing unit(s) 510 retrieves instructions to execute and data to process in order to execute the processes of some embodiments.

The bus 505 also connects to the input and output devices 530 and 535. The input devices enable the user to communicate information and select commands to the electronic system. The input devices 530 include alphanumeric keyboards and pointing devices (also called "cursor control devices", such as a mouse or a stylus). The output devices 535 display images generated by the electronic system 500. The output devices 535 include printers and display devices, such as cathode ray tubes (CRT) or liquid crystal displays (LCD). Some embodiments include devices such as a touchscreen that functions as both input and output devices.

Finally, as shown in FIG. 5, bus 505 also couples electronic system 500 to a network 540 through a network adapter (not shown), which may include wired or wireless network connectivity. In this manner, the computer can be a part of a network of computers (such as a local area network ("LAN"), a wide area network ("WAN"), or an intranet), or a network of networks (such as the Internet). Any or all components of electronic system 500 may be used in conjunction with the invention.

These functions described above can be implemented in digital electronic circuitry, in computer software, firmware or hardware. The techniques can be implemented using one or more computer program products. Programmable processors and computers can be packaged or included in mobile devices. The processes may be performed by one or more programmable processors and by one or more set of programmable logic circuitry. General and special purpose computing and storage devices can be interconnected through communication networks.

Some embodiments include electronic components, such as microprocessors, storage and memory that store computer program instructions in a machine-readable or computer-readable medium (alternatively referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media may store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the invention has been described with reference to numerous specific details, one of ordinary skill in the art will recognize that the invention can be embodied in other specific forms without departing from the spirit of the invention. For instance, FIG. 2 conceptually illustrates a process/method in which the specific operations of this method or process may not be performed in the exact order shown and described. Specific operations may not be performed in one continuous series of operations, and different specific operations may be performed in different embodiments. Furthermore, the method or process could be implemented using several sub-processes or sub-methods that are loadable as separate modules and run in connection with a main process to interconnect with other associated modules, or as part of a larger macro process. Thus, one of ordinary skill in the art would understand that the invention is not to be limited by the foregoing illustrative details, but rather is to be defined by the appended claims.

I claim:

1. A smartphone and tympanometer-based middle ear abnormality detection mobile system comprising:
   a smartphone with a mobile computing device operating system;
   a tympanometer with a USB terminal, a tympanometer pressure pump and power source, and a tympanometer probe that fits into an ear of a patient and is configured to capture data for admittance readings and data for pressure readings ("admittance and pressure data") while the tympanometer pressure pump exerts varying amounts of pressure into the ear of the patient;
   a USB cable that directly connects the smartphone to the tympanometer at the USB terminal, wherein the admittance and pressure data is sent directly from the tympanometer over the USB cable to the smartphone; and
   a software application installed on the smartphone and configured to (i) send a start signal over the USB cable to the tympanometer to start a tympanometer test, (ii) receive the admittance and pressure data sent over the USB cable by the tympanometer in relation to the tympanometer test, (iii) read the admittance and pressure data provided by the tympanometer, (iv) build a tympanogram that plots admittance data at different pressure readings, (v) analyze the tympanogram in comparison with tympanograms associated with a plurality of different types of middle ear infections, (vi) determine whether the patient has a middle ear infection based on the analyzed tympanogram, and (vii) visually output the tympanogram, textual data corresponding to the tympanogram, and a tympanogram test result that indicates only one a normal non-infected ear of the patient and a particular type of middle ear infection detected in the patient.

2. The smartphone and tympanometer-based middle ear abnormality detection mobile system of claim 1, wherein the software application comprises a user interface to selectively choose to start the tympanometer and analyze tympanometer test readings of the patient.

3. The smartphone and tympanometer-based middle ear abnormality detection mobile system of claim 2, wherein the user interface visually outputs the tympanogram on the screen of the smartphone based on the admittance and pressure data provided by the tympanometer.

4. The smartphone and tympanometer-based middle ear abnormality detection mobile system of claim 1 further comprising a machine learning module that continually updates an analysis module for analyzing tympanograms of patients.

5. A method for detecting middle ear abnormalities by a mobile computing device coupled to a tympanometer comprising:

starting a tympanometer software application installed on a smartphone mobile device that is physically connected by a USB cable to a tympanometer, wherein the tympanometer software application is configured to determine whether a patient has a middle ear infection by directing the tympanometer to test ear function in the patient;

receiving a selection of a particular graphical button among a plurality of graphical buttons in a user interface of the tympanometer software application, wherein the particular graphical button is configured to direct the tympanometer to start a tympanometer test when the tympanometer is positioned in an ear of the patient;

triggering the tympanometer to start a pressure test of the ear of the patient;

receiving, by the smartphone mobile device directly over the USB cable from the tympanometer, admittance and pressure data captured by the tympanometer during the pressure test;

generating a tympanogram based on the admittance and pressure data; and analyzing the tympanogram to determine ear function health in the patient.

6. The method of claim 5 further comprising identifying a selection of a second graphical button that is different from the particular graphical button in the plurality of graphical buttons, wherein the second graphical button comprises an analyze tympanogram graphical button.

7. The method of claim 6, wherein the plurality of graphical buttons comprises a start tympanometer graphical button, the analyze tympanogram graphical button, and a machine learning algorithm.

8. The method of claim 7, wherein the particular graphical button is the start tympanometer graphical button.

9. The method of claim 8, wherein triggering the tympanometer to start the pressure test of the ear of the patient comprises sending a command over the USB cable from the smartphone mobile device to the tympanometer to start the tympanometer.

10. The method of claim 9, wherein generating the tympanogram comprises receiving a selection of a patient type for the patient, wherein said patient type comprises one of a child patient and an adult patient, wherein analyzing the tympanogram comprises accounting for the selected patient type.

\* \* \* \* \*